United States Patent [19]

Larock

[11] Patent Number: 4,647,666

[45] Date of Patent: Mar. 3, 1987

[54] HETEROCYCLIC SYNTHESIS VIA THALLATION AND SUBSEQUENT PALLADIUM-PROMOTED OLEFINATION

[75] Inventor: Richard C. Larock, Ames, Iowa

[73] Assignee: Iowa State University Research Foundation, Inc., Ames, Iowa

[21] Appl. No.: 755,000

[22] Filed: Jul. 15, 1985

Related U.S. Application Data

[63] Continuation-in-part of Ser. No. 718,649, Apr. 1, 1985.

[51] Int. Cl.[4] ............................................. C07D 217/24
[52] U.S. Cl. ................................... 546/141; 548/510; 549/290; 549/283; 549/269; 549/408
[58] Field of Search ............... 549/283, 269, 141, 408, 549/290; 548/510

[56] References Cited

U.S. PATENT DOCUMENTS

| | | | |
|---|---|---|---|
| 2,615,024 | 10/1952 | Clinton et al. | 549/283 |
| 3,585,214 | 6/1971 | Boschetti et al. | 549/289 |
| 3,636,004 | 1/1972 | Bode et al. | 549/283 |
| 3,784,600 | 1/1974 | von Strandtmann et al. | 549/289 |
| 3,803,175 | 4/1974 | Sparks et al. | 549/283 |
| 3,803,857 | 4/1974 | Townend et al. | 549/283 |
| 3,808,232 | 4/1974 | Hardt et al. | 549/283 |
| 4,162,326 | 7/1979 | Milhailovski | 549/289 |
| 4,235,781 | 11/1980 | Kaufman | 549/289 |
| 4,279,823 | 7/1981 | Larock | 549/280 |
| 4,296,039 | 10/1981 | Della Valle | 549/289 |
| 4,312,883 | 1/1982 | Baccichetti et al. | 549/289 |
| 4,803,857 | 4/1978 | Townend et al. | 549/283 |

OTHER PUBLICATIONS

Larock, Tetrahedron Letters, vol. 25, No. 40, pp. 4459-4462, 1984.
Larock, R. C.; Varaprath, S.; Fellows, C. A. *J. Am. Chem. Soc.* 1984, 106, 0000.
Horino, H.; Inoue, N. *Heterocycles* 1978, 11, 281.

*Primary Examiner*—Jane T. Fan
*Attorney, Agent, or Firm*—Zarley, McKee, Thomte, Voorhees & Sease

[57] ABSTRACT

Functionally substituted arenes selected from the group consisting of p-tolylacetic acid, N-methylbenzamide, benzamide and acetanilide which are thallated provide an organothallium salt which undergoes subsequent palladium promoted olefination to provide oxygen and/or nitrogen heterocycles such as ethers lactones, isoquinolones, indoles and isocarbostyrils.

8 Claims, No Drawings

HETEROCYCLIC SYNTHESIS VIA THALLATION AND SUBSEQUENT PALLADIUM-PROMOTED OLEFINATION

GRANT REFERENCE

The invention described herein was made in part in the course of work under a grant from the National Institutes of Health No. GM 24254.

CROSS REFERENCE TO A RELATED APPLICATION

This application is a continuation-in-part of application Ser. No. 718,649, filed Apr. 1, 1985, in the name of the same inventor as a joint inventor, and entitled SYNTHESIS OF ISOCOUMARINS VIA THALLATION-OLEFINATION OF ARENES. The specification of the parent application is incorporated herein by reference.

BACKGROUND OF THE INVENTION

In the parent application it was discovered that isocoumarins and 3,4-dihydroisocoumarins could be prepared by the thallation and subsequent palladium promoted olefination of benzoic acid derivatives to provide a highly convenient new route to a variety of known biologically active compounds. In the process of the above referenced parent application, the starting material was either benzoic acid or a substituted benzoic acid. It has now been discovered that the basic process of that parent application can be expanded to conduct a very similar reaction with functionally substituted arenes to provide a variety of important oxygen and nitrogen heterocycles, namely certain ethers and lactones, isoquinolones, indoles and isocarbostyrils. All of these compounds are known to be of keen biological interest. For example, lactones are known to be odor bearing components of many plants, and as such have found wide industrial uses in the perfume industry. Certain lactones are also useful as solvents, paint removers, vapor sterilants and disinfectants. Isoquinolones are known to be useful in the manufacture of pharmaceuticals (such as nicotinic acid), insecticides, rubber accelerators, and anti-malarials. Indoles are known to be useful in perfumery, in agriculture and horticulture as growth enhancers, in some instances as flavorings, and indole alkaloids are known as especially physiologically active.

It therefore can be seen that there is a continuing need for the development of processes of preparing these useful compounds by a convenient and efficient synthesis.

It is a primary objective of the present invention to provide an improved one pot process for the preparation of certain ethers and lactones, isoquinolones, indoles and isocarbostyrils from functionally substituted arenes.

It is a further object of the present invention to prepare the above referred to oxygen and nitrogen heterocycles from simple olefins, dienes, allylic halides, vinyl halides, and unsaturated esters, by reacting functionally substituted arenes with an electrophilic thallium salt to provide an arylthallium intermediate compound which in turn is reacted with a palladium salt and the olefin, diene, allylic halide, vinyl halide, or unsaturated ester to provide the desired oxygen and/or nitrogen heterocyclic, such as an indole or an isoquinolone.

The method and manner of accomplishing each of the above objectives as well as others will become apparent from the detailed description of the invention which follows.

SUMMARY OF THE INVENTION

Thallation and subsequent palladium-promoted olefination of p-tolylacetic acid, N-methylbenzamide, benzamide and acetanilide provides a new route to a variety of important oxygen and nitrogen heterocycles such as certain ethers and lactones, isoquinolones, indoles and isocarbostyrils. In particular the process involves reacting a functionally substituted arene with an electrophilic thallium salt, in the presence of an organic solvent to provide a thallated intermediate compound. This intermediate is in turn reacted with an olefin, in the presence of a palladium salt to provide in a simple, one pot process the desired oxygen and nitrogen heterocycles.

DETAILED DESCRIPTION OF THE INVENTION

As earlier stated, this application is a continuation-in-part of my earlier co-pending and commonly assigned application Ser. No. 718,649, filed Apr. 1, 1985, entitled SYNTHESIS OF ISOCOUMARINS VIA THALLATION-OLEFINATION OF ARENES. The earlier application related to thallation and subsequent palladium promoted olefination of benzoic acids to provide a highly convenient new route to a variety of biologically active isocoumarins and 3,4-dihydroisocoumarins. Generally, the reactions of that earlier application can be summarized by the following reaction scheme, in which R represents any organic moiety.

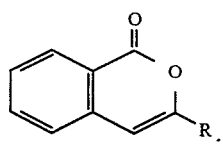

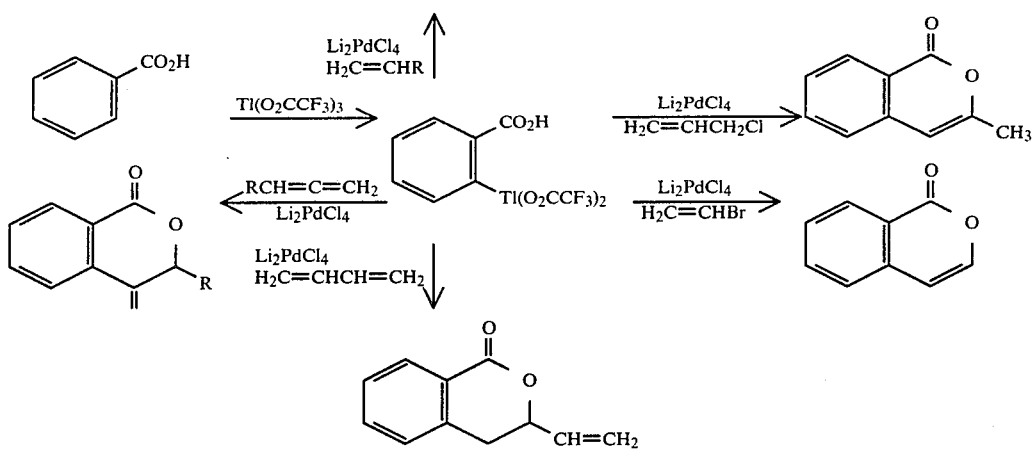

In the earlier reported synthesis, the first step thallation reaction was conducted in the presence of an electrophilic thallium salt. The reaction of the present invention is also conducted in the presence of the same electrophilic thallium salt, preferably thallium(III) trifluoroacetate. The second step of the two step reaction sequence, the palladium promoted olefination step, was previously and is here preferably conducted in the presence of an organic solvent, with the preferred solvents being methylene chloride and acetonitrile.

In the present reaction, the benzoic acid starting material of the earlier application is replaced with a functionally substituted arene containing either an oxygen or nitrogen functionality. In particular, the most preferred starting materials are p-tolylacetic acid, N-methylbenzamide, benzamide, acetanilide and m-methoxybenzyl alcohol. Among those above listed functionally substituted arenes, the precise arene used in this initial starting step is not critical and is simply representative of the wide variety of arenes which should be applicable in the process. Generally, however, the most satisfactory results are achieved when the arene is a $C_{12}$ or less structure and most preferably a $C_6$ to $C_{12}$ structure. When the arene is p-tolylacetic acid, the resulting products are lactones. When the arene is N-methylbenzamide, the end products are unsaturated lactams such as isoquinolones. When the arene is benzamide the end product is an isocarbostyril and, when the arene is acetanilide the end products are indoles. Benzylic alcohols give rise to cyclic ethers.

The electrophilic thallium salt employed is not critical, the essential factor simply being that the anion must be one which tends to make the thallium ion sufficiently reactive with respect to the aromatic ring. Suitable anions have been found to be trifluoroacetate, perchlorate, nitrate and acetate. Because of the ease of formation and availability, it is preferred that the electrophilic thallium compound be thallium trifluoroacetate. For details with respect to preparation of thallium trifluoroacetate, see McKillop, et al. *J. Am. Chem. Soc.*, Vol. 93, p. 4841–4844 (1971) which is incorporated herein by reference. The solvent employed in this first reaction step is not critical, and generally may be any solvent which will suitably dissolve the thallium compound and starting aromatic compound. Suitable solvents are preferably polar solvents such as trifluoroacetic acid, tetrahydrofuran, and acetic acid, or less polar solvents such as ether, methylene chloride and chloroform. Of course, others such as acetonitrile may also be employed conveniently.

The reaction temperature and pressure are not critical factors. Generally, the reaction may be run at any temperature from −20° C. up to 100° C., with the temperature of refluxing trifluoroacetic acid ( 72° C.) being satisfactory. The reaction time varies depending upon the reactivity of the starting aromatic compound and can be from a few minutes, up to as long as 96 hours. Commonly, a 24–48 hour thallation reaction time is sufficient.

After the initial formation of the aryl thallium intermediate compound, if desired, the salt may be isolated by removing the solvent under vacuum and recrystallizing. It is, however, not necessary to even isolate the intermediate unless one has a specific desire to do so. If isolation of the intermediate is not deemed important, the reaction can directly proceed to its second phase which involves removing the original solvent (usually trifluoroacetic acid), adding a new solvent (usually acetonitrile or methylene chloride), and reacting the arylthallium intermediate compound with an unsaturated organic compound selected from the group consisting of simple olefins, dienes, allylic halides, vinyl halides, and unsaturated esters, with the reaction occurring in the presence of a palladium halide salt.

Generally, the first phase of the reaction, that is the thallation reaction, may be represented by the following typical equation for example 7 as reported below, using acetanilide as the starting material.

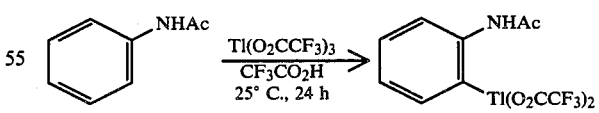

The second phase of the reaction may be typically illustrated for example 7 below by the reaction of the thallated acetanilide with allyl chloride to provide an indole as represented by the following equation.

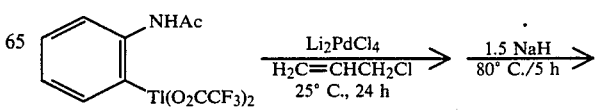

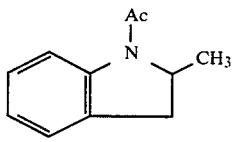

It can be seen that the reaction yields an indole. Investigation of this reaction and similar ones with various solvents has revealed that the preferred solvents are acetonitrile and methylene chloride. With regard to the olefin reaction, it is preferred that the olefin be a $C_2$ to $C_{12}$ monosubstituted terminal olefin or a disubstituted internal olefin of $C_4$ to $C_{12}$ chain length. Generally it can be said that the more highly substituted the double bond, the less reactive it will be. It is therefore preferred that the olefin be as little substituted as possible.

It can also be seen from the above reaction that it is essential that the reaction be conducted in the presence of a palladium salt, preferably a palladium halide salt and most preferably palladium chloride. The palladium salt is necessary for the cyclization reaction to occur. The scheme by which it is believed that this occurs is disclosed in a paper on this same topic, Larock et al., J. Am. Chem. Soc., 1984, 106, 5274 at p. 5275, which is incorporated herein by reference. Basically, while not wishing to be bound by any theory of operation during the process, the palladium(II) salt reacts with the organothallium intermediate to generate an organopalladium intermediate and a thallium(III) salt. The organopalladium intermediate then adds to the olefin double bond and either eliminates a beta hydride or beta halide to give a styrene intermediate. The palladium hydride is reduced to palladium(O), but the thallium-(III) salt formed in the initial transmetalation step apparently reoxidizes the palladium(O) to palladium(II), which then promotes intramolecular palladation of the styrene intermediate. A second palladium hydride elimination affords the end product. At this stage, the palladium has once again been reduced to palladium(O) and all of the reoxidant has also been used up. The overall reaction therefore requires one palladium per arene. When olefins bearing halogens, such as vinyl bromide or allyl chloride, are employed, the palladium is only reduced to palladium(O) once and so the reaction becomes catalytic in palladium (the thallium can continually reoxidize it).

However, the amount of palladium salt employed is generally an equimolar amount with the amount of thallated arene employed.

In the preferred process one may use two equivalents of olefin, and either acetonitrile or methylene chloride is the preferred solvent. It is also preferred that one adds two equivalents of potassium carbonate plus two equivalents of triethylamine in the olefination reaction. This seems to promote cyclization and increase the yield of product in some instances.

The following examples are offered to further illustrate but not limit the process of the present invention (see Table I).

In each of the examples, the following general procedure was employed for the thallation of the functionally substituted arenes. Since the number of examples is so voluminous it will, for efficiency purpose, serve to show the general procedure for the thallation of benzoic acid itself with the understanding that an identical or similar procedure was employed with each of the functionally substituted arenes prepared in accordance with the table shown below.

General Procedure

Thallium(III) oxide (25 g) was weighed into a 250 ml round bottom flask and trifluoroacetic acid (100 ml) was then added and the mixture was stirred vigorously. A reflux condenser was attached, and water (12 ml) was added through the top of the condenser. The flask was wrapped with aluminum foil and the mixture was refluxed overnight (12-19h). Filtration of the reaction mixture while still hot through a coarse sintered-glass Buchner funnel into a weighed 250 ml round bottom flask removed any residual brown or yellow solid. The colorless solution was concentrated as much as possible on a rotary evaporator. Usually, white solid could be observed in the flask at this stage. The last traces of solvent were removed on a vacuum pump. The thallium(III) trifluoroacetate thus produced was a white solid. Yields ranged from 95-99%. The reagent was stored under $N_2$ in a stoppered round bottom flask wrapped in aluminum foil. Exposure to warm, moist air caused the white solid to become brown and sticky.

The reagent was transferred in a glove bag under $N_2$ to a preweighed flask and then dissolved in the appropriate amount of trifluoroacetic acid prior to each experiment.

To a solution of 16.0 g (29.4 mmol) of thallium(III) trifluoroacetate in 58 ml of trifluoroacetic acid was added 3.97 g (29.4 mmol) of N-methylbenzamide. The reaction mixture was refluxed 36 hours. The mixture was cooled and the solvent was evaporated to afford 17.1 g of thallated N-methylbenzamide (see Table I, entry 4): yield 100%.

The following is the general procedure used for olefination of the thallated N-methylbenzamide compound. To a solution of 0.2823 g (0.5 mmol) of thallated N-methylbenzamide, 0.0887 g (0.5 mmol) of palladium chloride, and 0.0425 g. (1 mmol) of lithium chloride in 6 ml of dry acetonitrile was added along with the appropriate olefin, (1 mmol; except for ethylene and vinyl bromide, they were used in large excess). The mixture was stirred at room temperature for 16-18 h and then heated under reflux for 5 h. After being cooled to room temperature, the reaction mixture was filtered through diatomaceous earth. The diatomaceous earth pad was washed with 100 ml of ether. The filtrate and washing were combined and washed twice with saturated ammonium chloride solution. The organic layer was separated, dried (MgSO$_4$), and concentrated. The reaction products were isolated by flash chromatography on a silica gel (230-400 mesh) column.

The olefination of thallated N-methylbenzamide with 3-chloro-1-propene gave only one isolable product (see Table I, entry #4): yield 61%; $^1$H NMR (CDCl$_3$) Δ2.37 (s, 3 H, CH$_3$), 3.55 (s, 3 H, NCH$_3$), 6.30 (s, 1 H, C=CH), 7.18-7.74 (m, 3 H, ArH), 8.24-8.47 (m, 1 H, ArH); IR (HCC$_3$) 1650 (C=O), 1620 (C=C) cm$^{-1}$; mass spectrum, m/z calcd for C$_{11}$H$_{11}$NO 173.08407, obsd 173.08366.

EXAMPLES 1-9

Each of the examples reported in Table 1 follow the just presented representative procedure for example 4, but with the variations indicated in the column entitled "Olefination Conditions".

Thallation of the arenes listed in Table 1 was accomplished using the following variations of other earlier published procedures of Larock, R. C.; Varaprath, S.; Lau, H. H.; Fellows, C. A. *J. Am. Chem. Soc.* 1984, 106, 5274; McKillop, A.; Hunt, J. D.; Zelesko, M. J.; Fowler, J. S.; Taylor, E. C.; McGillivray, G.; Kienzle, F. *J. Am. Chem. Soc.* 1971, 93, 4841; and Taylor, E. C.; Kienzle, F.; Robey, R. L.; McKillop, A.; Hunt, J. D. *J. Am. Chem. Soc.* 1971, 93, 484, which are incorporated herein by reference. p-Tolylacetic acid (25° C., 48 h), N-methylbenzamide (reflux, 36 h), benzamide (reflux, 24 h), acetanilide (25° C., 48 h), m-methoxybenzyl alcohol (arene addition at 0° C., 25° C. overnight). The resulting organothallium compounds were allowed to crystallize from solution and were reacted further as indicated in footnote a in Table 1, with the variations indicated under "Olefination Conditions".

TABLE I.

Heterocyclic Synthesis via Thallation and Subsequent Palladium-Promoted Olefination[a]

| Entry | Thallated Arene | Olefin (2 equiv) | Olefination Conditions[a] | Product | % Isolated Yield |
|---|---|---|---|---|---|
| 1 | 2-CH₂CO₂H, 5-CH₃, Tl(O₂CCF₃)₂ benzene | H₂C=CHCH(CH₃)₃ | CH₂Cl₂; 2Et₃N/2K₂CO₃/50° C./5 h | isochroman-1-one with CH₂C(CH₃)₃ and CH₃ | 77 |
| 2 | same as 1 | H₂C=CHCO₂CH₃ | 0.1 Li₂PdCl₄/48 h; Et₃N/Δ | isochroman-1-one with CH₂CO₂CH₃ and CH₃ | 71 |
| 3 | same as 1 | H₂C=CHCH=CH₂ | CH₂Cl₂; 2Et₃N/2K₂CO₃/50° C./5 h | benzoxepinone with CH=CH₂ and CH₃ | 69 |
| 4 | 2-CONHCH₃, Tl(O₂CCF₃)₂ benzene | H₂C=CHCH₂Cl | —; 80° C./5 h | N-methyl isoquinolinone with CH₃ | 61 |
| 5 | same as 4 | H₂C=CHCO₂CH₃ | —; 1.5 NaH/80° C./5 h | N-methyl isoquinolinone with CHCO₂CH₃ | 52 |
| 6 | 2-CONH₂, Tl(O₂CCF₃)₂ benzene | H₂C=CHCH₂Cl | —; Δ/5 h | isoquinolin-1-ol with CH₃ | 60 |

TABLE I.-continued

Heterocyclic Synthesis via Thallation and Subsequent Palladium-Promoted Olefination

| Entry | Thallated Arene | Olefin (2 equiv) | Olefination Conditions[a] | Product | % Isolated Yield |
|---|---|---|---|---|---|
| 7 | 2-NHAc, Tl(O$_2$CCF$_3$)$_2$ substituted benzene | H$_2$C=CHCH$_2$Cl | —; 1.5 NaH/80° C./5 h | N-Ac-2-methylindole | 45 |
| 8 | 2-NHAc, Tl(O$_2$CCF$_3$)$_2$ substituted benzene | H$_2$C=CHBr | —; 1.5 NaH/80° C./5 h | N-Ac-indole | 45 |
| 9 | 4-CH$_3$O, 2-CH$_2$OH, Tl(O$_2$CCF$_3$)$_2$ substituted benzene | cis-H$_2$C=CHCH=CHCH$_3$ | CH$_2$Cl$_2$/20 h; 2Et$_3$N/2Na$_2$CO$_3$/Δ/5 h | 5-CH$_3$O-substituted isochromene with CH=CHCH$_3$ side chain | 54 |

[a]Olefination was carried out using 1 equiv Li$_2$PdCl$_4$ in CH$_3$CN at 25° C. for 16 h unless otherwise indicated; base and/or heat were then introduced as indicated.

It can be seen that the thallation-olefination of benzamides and acetanilides in particular would appear to be a particularly valuable route to the isocarbostyril, isoquinolone and indole ring systems. The compounds prepared were successfully isolatable in high yield and the reaction is essentially a one pot process reaction. It can therefore be seen that the invention accomplishes at least all of the state objectives.

What is claimed is:

1. A method of preparing oxygen and nitrogen containing heterocycles, which are selected from the group consisting of ethers, lactones, isoquinolones, indoles and isocarbostyrils, comprising:

reacting a functionally substituted arene selected from the group consisting of p-tolylacetic acid, N-methylbenzamide, benzamide, acetanilide, and m-methoxybenzyl alcohol with an electrophilic thallium salt in the presence of an organic solvent to provide an arylthallium intermediate compound; and reacting said arylthallium intermediate with an olefin selected from the group consisting of a $C_2$ to $C_{12}$ terminal olefin, a $C_3$ to $C_{12}$ diene, allylic halide, vinyl halide, and a $C_2$ to $C_{12}$ unsaturated ester, said reaction occurring in the presence of a palladium salt to yield a heterocyclic product.

2. The process of claim 1 wherein said palladium salt is a palladium halide salt.

3. The process of claim 2 wherein said palladium salt is dilithium tetrachloropalladate, $Li_2PdCl_4$.

4. The process of claim 1 wherein said olefin is a vinyl halide.

5. The process of claim 1 wherein said olefin is an unsaturated ester.

6. The process of claim 1 wherein said olefin is an allylic halide.

7. The process of claim 1 wherein said olefin is a diene.

8. The process of claim 1 wherein the solvent for said reaction is selected from the group consisting of methylene chloride and acetonitrile.

* * * * *